(12) United States Patent  
Imran et al.

(10) Patent No.: US 10,542,924 B2  
(45) Date of Patent: Jan. 28, 2020

(54) DEVICE, SYSTEM AND METHODS FOR MEASUREMENT OF PRESSURES IN THE URINARY TRACT

(71) Applicant: InCube Labs, LLC, San Jose, CA (US)

(72) Inventors: Mir Imran, Los Altos Hills, CA (US); Ben Tranchina, Boerne, TX (US)

(73) Assignee: InCube Labs, LLC, San Jose, CA (US)

( * ) Notice: Subject to any disclaimer, the term of this patent is extended or adjusted under 35 U.S.C. 154(b) by 639 days.

(21) Appl. No.: 15/153,314

(22) Filed: May 12, 2016

(65) Prior Publication Data

US 2016/0331294 A1    Nov. 17, 2016

Related U.S. Application Data

(60) Provisional application No. 62/160,201, filed on May 12, 2015.

(51) Int. Cl.
*A61B 5/20* (2006.01)
*A61N 1/05* (2006.01)
(Continued)

(52) U.S. Cl.
CPC ............ *A61B 5/205* (2013.01); *A61B 5/6853* (2013.01); *A61N 1/0551* (2013.01);
(Continued)

(58) Field of Classification Search
CPC ...... A61M 25/0017; A61M 2025/0037; A61M 2025/0031; A61M 2025/0003; A61B 5/205; A61B 5/6853
See application file for complete search history.

(56) References Cited

U.S. PATENT DOCUMENTS

| 5,385,563 A | 1/1995 | Gross |
| 6,447,462 B1 | 9/2002 | Wallace et al. |

(Continued)

FOREIGN PATENT DOCUMENTS

| WO | WO 9918851 A1 * | 4/1999 | ......... A61B 5/04882 |
| WO | WO-2012122267 A1 | 9/2012 | |
| WO | WO-2014104689 A1 | 7/2014 | |

OTHER PUBLICATIONS

PCT/US2016/032203 International Search Report and Written Opinion dated Aug. 12, 2016.

(Continued)

*Primary Examiner* — Sean P Dougherty
(74) *Attorney, Agent, or Firm* — Wilson Sonsini Goodrich and Rosati, P.C.; Joel M. Harris (57) ABSTRACT

A catheter for measuring pressure in the urinary tract of a patient includes a catheter body having a proximal and distal end. A plurality of lumens is formed in the catheter body, and an adaptor is coupled to the proximal end of the catheter body. The adaptor includes a port for each lumen. A first pressure sensor, typically including a balloon, is fluidically coupled to a first lumen and is configured and positioned to measure pressure in a urethra of the patient. A second pressure sensor, also typically including a balloon, is fluidically coupled to a second lumen and is configured and positioned on the catheter body to measure pressure in a bladder of the patient. An expandable retention member, which may be coupled to a third lumen, is positioned on the catheter body between the first and second expandable pressure sensors so that the catheter body may be retained at a selected location in the urinary tract to properly position the fluid pressure sensors in the bladder and urethra, respectively.

28 Claims, 3 Drawing Sheets

(51) Int. Cl.
*A61B 5/00* (2006.01)
*A61M 25/00* (2006.01)

(52) U.S. Cl.
CPC . *A61M 25/0026* (2013.01); *A61M 2025/0031* (2013.01); *A61M 2025/0037* (2013.01); *A61M 2210/1078* (2013.01)

(56) References Cited

U.S. PATENT DOCUMENTS

| | | |
|---|---|---|
| 6,997,884 B2 | 2/2006 | Ulmsten et al. |
| 2009/0306539 A1* | 12/2009 | Woodruff ............... A61B 5/205 600/561 |
| 2012/0035595 A1 | 2/2012 | Goedje et al. |
| 2013/0030262 A1* | 1/2013 | Burnett ............... A61B 5/0215 600/309 |
| 2015/0257695 A1* | 9/2015 | Addington ............. A61B 5/205 600/301 |

OTHER PUBLICATIONS

European search report with written opinion dated Dec. 7, 2018 for EP16793560.

* cited by examiner

FIG. 4A   FIG. 4B

DEVICE, SYSTEM AND METHODS FOR MEASUREMENT OF PRESSURES IN THE URINARY TRACT

CROSS-REFERENCE TO RELATED APPLICATIONS

This application claims the benefit of priority to U.S. provisional Application No. 62/160,201, filed May 12, 2015, the entire content of which is incorporated herein by reference for all purposes.

BACKGROUND OF THE INVENTION

1. Field of the Invention

Embodiments described herein relate to devices, systems and methods for measurement of pressure in the urinary tract. More specifically, embodiments described herein relate to a device, such as a catheter, positionable within the urinary tract (UT) for measurement of pressure in one or more locations in the UT such as the bladder and urethra. Still more specifically embodiments described herein relate to a catheter positionable within the urinary tract for measurement of pressures within the bladder and urethra to facilitate placement of a neuromodulation device within the urinary tract for treatment of an overactive bladder.

Urinary incontinence can be a common and distressing problem, which may have a profound impact on quality of life but which is often underreported. In many cases, urinary incontinence results from an underlying treatable medical condition. Urinary incontinence arises in both men and women, with varying degrees of severity, and from different causes. In men, the condition most frequently occurs as a result of prostatectomies which result in mechanical damage to the urethral sphincter. In women, urinary incontinence typically develops after pregnancy when musculoskeletal damage has occurred as a result of inelastic stretching of the structures which support the genitourinary tract. Specifically, pregnancy can result in inelastic stretching of the pelvic floor, the external sphincter, and the tissue structures which support the bladder and bladder neck region. In each of these cases, urinary leakage typically occurs when a patient's abdominal pressure increases as a result of stress, e.g., coughing, sneezing, laughing, exercise, or the like.

Treatment of urinary incontinence can take a variety of forms though each has drawbacks. Most simply, the patient can wear absorptive devices or clothing, which is often sufficient for minor leakage events. Alternatively or additionally, patients may undertake exercises intended to strengthen the muscles in the pelvic region, or may attempt a behavior modification intended to reduce the incidence of urinary leakage.

In cases where such non-interventional approaches are inadequate or unacceptable, the patient may undergo surgery to correct the problem. A wide variety of procedures have been developed to correct urinary incontinence in women. Several of these procedures are specifically intended to support the bladder neck region. For example, sutures, straps or other artificial structures are often looped around the bladder neck and affixed to the pelvis, the endo-pelvic fascia, the ligaments which support the bladder, or the like. Other procedures involve surgical injections of bulking agents, inflatable balloons, or other elements to mechanically support the bladder neck.

In another approach, a stimulatory lead electrode is positioned to modulate neural signals going to the bladder so as to decrease the symptoms from an over active bladder. However, current devices do not provide the surgeon with sufficient real time measurement of bladder and/or urinary sphincter pressure to assess the effectiveness of treatment.

Accordingly, there exists a need for improved devices and methods for measurement of pressures in the urinary tract.

BRIEF SUMMARY OF THE INVENTION

Various embodiments of the invention described herein provide devices (e.g., a catheter) systems and methods for measuring pressures at various locations in the urinary tract (UT). Many embodiments provide devices, systems and methods for measuring pressures at various locations in the urinary tract including for example the bladder. Still more specifically, embodiments provide devices, systems and methods for measuring pressures at various locations in the urinary tract so that the effectiveness of a urinary incontinence treatment can be evaluated. Particular embodiments provide a catheter positionable within the urinary tract for simultaneous and/or sequential pressure (or related) measurement in the bladder and urethra to facilitate placement of a neuromodulation stimulation electrode for treatment of urinary incontinence from an overactive bladder and other related conditions. Further, embodiments provide a method for real time measurement of pressures in the urinary tract including the bladder and urinary sphincter to assess the effectiveness of placement of stimulation lead electrode to neuro-modulate nerve impulses causing an over active bladder. As such, embodiments of the invention are particularly useful for improving the efficacy of various neuromodulation and other procedures for treatment of urinary continence and related conditions by providing real time quantitative and/or qualitative data for assessing placement of the stimulating electrode to produce the desired effect on the urinary tract.

One embodiment provides a catheter for measuring pressure in the urinary tract of a patient comprising a catheter body having a proximal and distal end and a plurality of lumens including at least a first, second and third lumen; an adaptor coupled to the proximal end of the catheter body, the adaptor including a plurality for ports including at least a first, second and third port for fluidic coupling to the plurality of lumens; a first pressure sensor fluidically coupled to the first lumen, the first pressure sensor configured and positioned on the catheter body to be positioned and measure pressure in a urethra of the patient; a second pressure sensor fluidically coupled to the second lumen, the second pressure sensor configured and positioned on the catheter body to be positioned and measure pressure in a bladder of the patient; and an expandable retention member fluidically coupled to the third lumen and positioned on the catheter body between the first and second expandable pressure sensors, the expandable retention member configured when in an expanded state to retain the catheter body at selected location in the urinary tract in response to a physiological force exerted on at least a portion of the catheter.

The retention member will typically comprise an expandable member such as an expandable balloon that is expanded through the third lumen and is configured to retain the catheter body at a selected location in the urinary tract (including retaining the first sensor in the urethra and the second sensor in the bladder, when subjected to one or more physiological forces including hydrostatic pressure from the bladder as well force resulting contraction of the bladder and/or contraction of the urinary sphincter.

The pressure sensors may correspond to a variety of pressure sensors known in the art including various solid state and/or a "MEMS" based sensors. "MEMS" refers to a class of micro-electro-mechanical systems which typically comprise micro-fabricated miniaturized mechanical and electro-mechanical elements (i.e., devices and structures). Also in preferred embodiments, the first or second pressure sensor comprises or is otherwise positioned on an expandable member such as expandable balloon which may be inflated by means of the first or second lumens. In such embodiments, the expandable balloon may coupled by means of the first or second lumen, to an external pressure sensor such as a manometer which is coupled to the catheter via means of one or more of the ports (e.g., the first or second ports). The expandable pressure sensors are advanced to their selected locations in a non-expanded state and then deployed to their expanded state once the catheter body is at a selected locations in the urinary tract. The expandable members/sensors also facilitate retention of the sensors at their respective locations in the urethra and bladder.

The catheter body may be fabricated from a variety of medical polymers known in the art including, for example, one or more of PEBAX, Polyethylene, HDPE (high density polyethylene), PET (polyethylene teraphalate), polyurethane and the like. In preferred embodiments, the catheter lumens have sufficient stiffness or hoop strength such that a change in pressure in one lumen does not cause a significant pressure change <5% preferably <2%). Such stiffness or hoop strength can be achieved by use of one or more of the catheter materials, a reinforcing braid (either internal or external to the lumen), or an internal re-enforcing member (e.g., an internal polyimide tube or other stiff polymer material known in the catheter arts which can include various radiated polymers materials known in the art such as various radiated polyethylenes both LDPE and HDPE).

Also, in various embodiments, the catheter can be configured for placement in either the male or female urinary tract. Such configurations may include one more of length, diameter stiffness, length and position of the respective sensors. According to one embodiment for the male anatomy, the first sensor, (the urethra pressure sensor) has a length of about 2 cm. According to another embodiment, for the female anatomy, the first sensor, (the urethra pressure sensor) has a length of about 1.5 cm. As used herein, the term "about" means within +/- 10% of a stated value for a parameter, measurement, dimension, characteristic, physical property and the like.

Embodiments of the invention are particularly useful for making pressure measurements at two more locations in the urinary tract such as the bladder and urethra so as to facilitate a procedure to treat an overactive bladder. In particular, this includes providing the doctor feedback (by means of the pressure measurements) during the procedure on the effectiveness of the treatment. The pressure measurements may be made substantially simultaneously or sequentially, so to have an indication of a response by one more of the bladder, and urethral sphincter to a particular form of treatment or treatment stimulus. Typically, such a procedure will comprise placement and/or electrical coupling of an electrical lead on an nerve enervating the bladder (e.g. the hypogastric plexuses and nerves, and the pelvic splanchnic nerves and the inferior hypogastric plexus) so as to provide an neuro-modulating signal that modulates or otherwise attenuates a nerve signal causing an unwanted contraction of the bladder. In another embodiment, the treatment for the overactive bladder may comprise the delivery of electrical stimulations to the patient's foot from one or more transcutaneous electrodes placed on the patients foot (e.g., the sole top portion, etc)

In an exemplary embodiment of using the invention, an embodiment of a pressure measurement catheter such as an embodiment described is advanced into the urinary tract (trans-vaginally for a woman, trans-penaly for a man) so as to position the first sensor at a first location in the urethra and the second sensor in the bladder. Advancement may be done under image guidance and proper placement determined by imaging and/or pressure measurements from the first and second sensor. Then once the catheter is placed at the desired location in the urinary tract, the retention member is inflated via the third lumen (or another lumen) so as to anchor or retain the catheter in place in response to once or more physiological forces including hydrostatic pressure from the bladder and/or a contractile force from one or more of the bladder or urethral sphincter. For embodiment having inflatable or otherwise expandable pressure sensor, one or both the sensor may be expanded before, after or about the same time as the retention member so as to retain the pressure sensors at their selected locations in the urethra or bladder. (They along with the retention member can be deflated for withdrawal of the catheter). Then pressure from the respective sensors can be takin over the course of a surgical or other procedure to treat an over active bladder. In particular, pressures may be measured (either simultaneously or sequentially) from both sensors in response to an external stimulus to assess the effectiveness of the treatment. In particular embodiments, that external stimulus may correspond to a neuro modulating electrical signal from an electrode electrically coupled to a nerve innervating the bladder (and causing unwanted contraction of the bladder) and/or the injection of fluid into the bladder from the pressure measurement catheter or another catheter. In either case, the pressure measurement signals allows the doctor to determine if the treatment has been effective by determining if unwanted bladder contraction are continuing to occur and/or what hydrostatic pressure in the bladder causes contraction. Multiple measurements may be taken over the course of the procedure (including before, during and after) to determine the effectiveness of treatment. For treatments involving the neuromodulation signal, the physician can use the pressure measurement to assess the effectiveness of one or both of the waveform of the neuro-modulation signal as well as the placement of the electrode to deliver the signal.

In related embodiments, pressure measurements can be made using embodiments of the pressure measurement catheter described herein to assess the effectiveness of treatment for overactive bladder comprising the delivery of pulsed electrical signals to the patients foot from a plurality of electrodes placed on the patient's foot (e.g., on the plantar or dorsal side adjacent metatarsal bones). Specifically, pressures in the bladder (and/or urethral sphincter) can be measured to determine a micturition volume threshold in the bladder and the effectiveness of the delivered pulsed electrical signals in increasing that threshold. The pressure measurements can be used to assist in one or more of electrode placement on the patient's foot and/or tune or fine tuning of the electrical signal waveform (e.g., in terms of pulse width, frequency, and amplitude) to optimize increases in the patient's micturition volume threshold. Micturition volume threshold (MVT) is defined herein as the volume of fluid in the bladder which results in a contraction and subsequent voiding of the bladder and thus it provides an indication of the effectiveness of treatment in reducing an overactive bladder. This is the case due to the fact that a reduction in an over active bladder should result in an increased micturition volume threshold. In one approach, MVT can be determined using an embodiment of the pressure measurement catheter to fill the bladder with fluid (e.g., through an irrigation lumen) and then monitor the delivered volume at which bladder contraction and subsequent voiding occurs. Typically, the electrical waveform will comprise a pulsed signal having a frequency ranging from about 1 Hz to 500 Hz a voltage ranging from about 1 V to 50V and pulse width from about 0.1 to 3 ms. Pressure measurements can be made using embodiments of the invention to tune and/or fine tune one or more of these signal parameters so as optimize the increase in micturition volume in the bladder in response to the delivery of the electrical signals. In use, such approaches enable better clinical outcomes for the patient with Further details of these and other embodiments and aspects of the invention are described more fully below, with reference to the attached drawing figures.

DETAILED DESCRIPTION OF THE INVENTION

Various embodiments described herein provide devices, apparatus and methods for measuring pressures at various locations in the urinary tract (UT). Many embodiments provide a devices, systems and methods for measuring pressures at various locations in the urinary tract including for example the bladder. Still more specifically embodiments provide devices, systems and methods for measuring pressures at various locations in the urinary tract so that the effectiveness of a urinary incontinence treatment can be evaluated. Particular embodiments provide a catheter positionable within the urinary tract for measurement of pressures within the bladder and urethra to facilitate placement of a neuromodulation stimulation electrode within the urinary tract for treatment of an over active bladder.

Figures 1, 2:
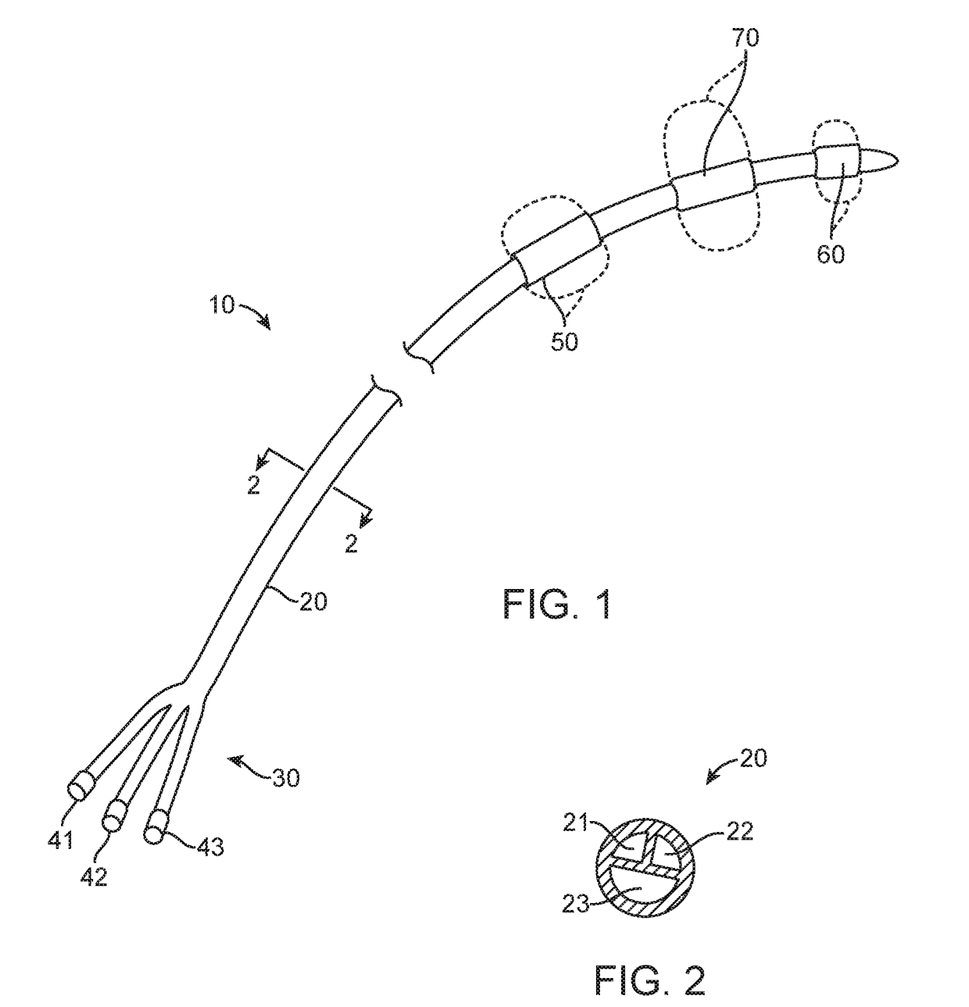
FIG. 1 illustrates an embodiment of a urinary tract pressure sensing catheter constructed in accordance with the principles of the present invention.
FIG. 2 is a cross-sectional view taken along line 2-2 in FIG. 1.

Referring now to FIG. 1, an embodiment of a catheter 10 for measuring pressure in the urinary tract includes a multi-lumen catheter body 20 having at least a first lumen 21, a second, lumen 22, and a third lumen 23 (FIG. 2), a proximal adapter 30 having one or more ports including at least a first port 41, a second port 42, and a third port 43; a first or urethral sphincter pressure sensor 50, a second or bladder pressure sensor 60, and an anchoring or retention member 70. Typically adaptor 30 will include at least three ports for coupling of one or more fluid lines (e.g. for irrigation and drainage), pumps, syringes, sensors, manometers, electrical cabling and the like, but ports are contemplated including a fifth and six port for other purposes. In particular, a fourth port may connect to a fourth lumen (not shown) which runs all the way to a distal tip of the catheter body 20 to permit fluid infusion and/or aspiration from the bladder.

The urethral sphincter pressure sensor 50 and the bladder pressure sensor 60 will typically include inflatable bladders where an inflation pressure can be monitored as a measure of physiologic pressure at the point of inflation. Pressure measurement transducers may be provided near the inflation source and/or within the inflatable bladders. Other locations are also considered. As the inflation region will be closed, the pressure at all points within the pressurized region will be virtually identical so long as the inflation medium is not flowing.

Figure 3:
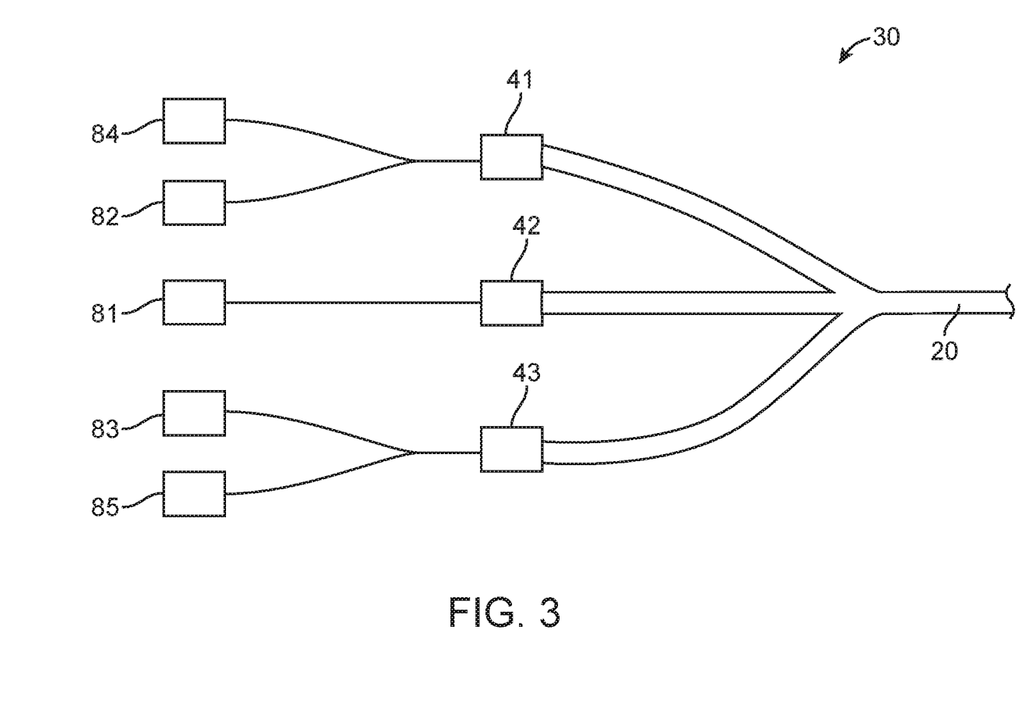
FIG. 3 is a detailed view of a proximal adaptor of the urinary tract pressure sensing catheter of FIG. 1, showing the connection to individual inflation source and pressure measurement sensors.

FIG. 3 shows an exemplary arrangement for inflating the inflatable bladders for both sensors 50 and 60 as well as the anchoring or retention member 70. In this arrangement, pumps 81, 82, and 83 are connected to ports 41, 42, and 43, respectively. The first pump 81, which may be a syringe, an insufflator, or any other common medical balloon inflation device known in the art, is used to inflate the anchoring or retention member 70 and may or may not include a pressure sensor (none is shown in FIG. 3). The second pump 82 is connected to inflate the inflatable bladder of the urethral sphincter pressure sensor 50 and includes a pressure transducer 84 which provides the pressure within the urethra U at the bladder sphincter. The third pump 83 is connected to inflate the inflatable bladder of the bladder pressure sensor 60 and includes a pressure transducer 85 which provides the pressure within the bladder. The pressure transducers may be simple mechanical gauges or may be solid state transducers that provide an electronic output. Manometers and other know medical pressure measurement devices could also find use.

Figure 4A:
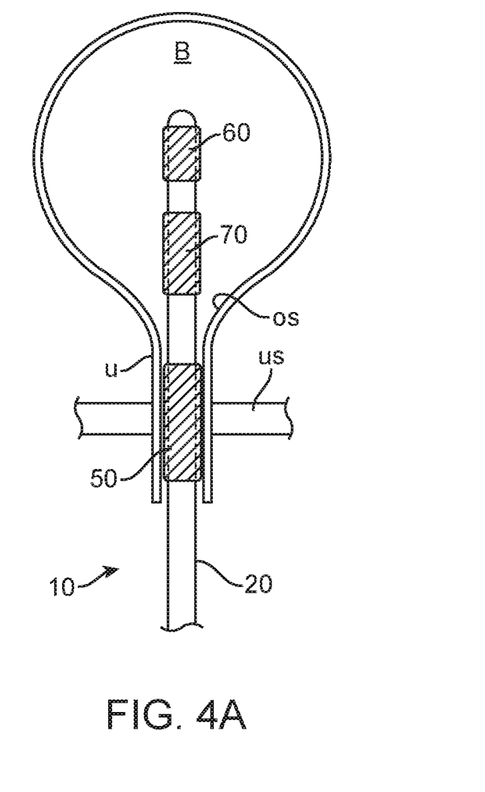
FIGS. 4A and 4B show use of the urinary tract pressure sensing catheter in measuring urinary tract pressure in a bladder and a urethra of a patient.

As shown in FIG. 4A, the catheter 10 is initially introduced trans-urethrally to position the uninflated sensors 50 and 60 and anchoring or retention member 70. The urethral sphincter sensor 50 is positioned to be inflated within and receive pressure readings from the sphincter muscle US when the anchoring or retention member 70 is inflated and drawn back against the bladder neck OS, as is typically done with a Foley catheter. The urethral sphincter sensor 50 has several embodiments. In one embodiment, it is split into two sections, one for the internal urethral sphincter and one for the external urethral sphincter. In the male version of the catheter the sensor is located approximately 2.5_cm distal to the bladder neck, and extends approximately 2.0 cm of urethral length. In the female version of the catheter the sensor is located approximately 1.8 cm distal to the bladder neck, and extends approximately 1.5 cm of urethral length. The bladder pressure sensor 60 extends a short distance distally of the anchoring or retention member 70 and is configured to remain in the center portion of the bladder B. The sensors and balloon are configured to be expandable and retractable such that during insertion or removal of the catheter they do not provide significant resistance (i.e., the catheter push or pull force is less than a selected value, e.g., less than 1.0 pound, more preferably less than 0.5 lbs, still more preferably less than 0.25 lbs).

According to one or more embodiments, the catheter body 20 may be sufficiently rigid (e.g., radial rigidity or stiffness) and/or may have sufficient hoop strength to prevent pressure changes in an individual lumen from significantly impacting the pressure in another lumen, e.g. any impact will result in a deviation below about 5%, preferably below about 2%. In other words, the lumens are configured to prevent hydrostatic pressure cross-talk from one lumen to the next. Preferably, though, the catheter as a whole will remain sufficiently compliant to be advanced and manipulated in and through the intended patient anatomy for the clinical use scenarios. In specific embodiments, the catheter lumens have sufficient stiffness or hoop stress such that any change in pressure in one lumen resulting from a change in an adjacent lumen will remain at or below, preferably below, about 5%, preferably 2%. Such stiffness or hoop strength can be achieved by any one or more of the following: (1) choice of catheter materials, (2) catheter/lumen dimensions, (3) use of a reinforcing braid (internal external to the lumen), and/or (4) an internal re-enforcing lumen. In various embodiments the radial rigidity (also described herein as radial stiffness), of any one of lumens 21, 22 and 23 (or other lumen of catheter 10) can be in the range of about 1 to about 100 N/mm, more preferably in a range of about 20 to about 100 N/mm and still more preferably in a range of about 50 to about 100 N/mm with specific embodiments of 5, 10, 20, 25, 30, 40, 45, 50, 55, 60, 70, 75, 80, 90 and 95 N/mm; whereas the hoop strength can be in a range of about 0.25 to 5 lbs, more preferably about 0.5 to 5 lbs, and still more preferably about 1 to 10 lbs, with specific embodiments of 0, 5, 1, 2, 2, 5, 3, 4, 5, 6, 7, 8 and 9 lbs of force.

Figure 4B:
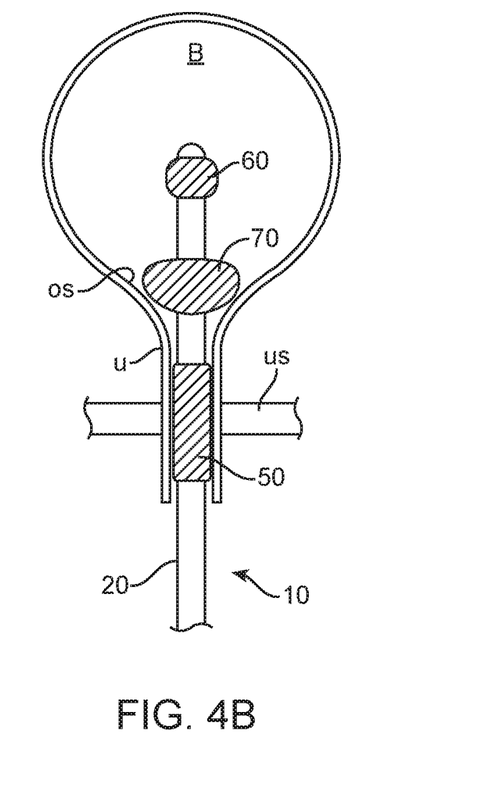

In an exemplary embodiment of a method of using the invention, an embodiment of a pressure measurement catheter 10 is advanced into the urinary tract (trans-vaginally for a woman, trans-penaly for a man) so as to position the first sensor 50 at a first location in the urethra U and the second sensor 60 in the bladder. Advancement may be done under image guidance, and proper placement may be determined by imaging and/or by pressure measurements using the first and/or second sensors 50 or 60. Once the catheter 10 is placed at the desired location in the urinary tract, the retention member 70 is inflated via the third lumen 23 (or another lumen) so as to anchor or retain the catheter 10 in place to inhibit movement in response to physiological forces such as hydrostatic pressure from the bladder B and/or a contractile force from one or more of the bladder or urethral sphincter. For embodiments having an inflatable or otherwise expandable pressure sensor, as illustrated, one or both the sensors 50 and 60 may be expanded before, after or about the same time as the retention member 70 to hold the pressure sensors at their selected locations in the urethra U or bladder. The sensors and the retention member can be deflated prior to withdrawal of the catheter.

Pressure from the sensors 50 and 60 can be taken continuously or periodically over the course of a surgical or other procedure to treat an overactive bladder or for any other purpose. In particular, pressures may be measured (either simultaneously or sequentially) from both sensors 50 and 60 in response to an external stimulus to assess the effectiveness of a treatment for an overactive bladder. In particular embodiments, external stimulus may effected by applying a neuro modulating electrical signal from an electrode electrically coupled to a nerve innervating the bladder to induce contraction of the bladder. Alternatively or additionally, fluid may be injected into the bladder, typically using a lumen in the pressure measurement catheter 10 or another catheter. In either case, pressure measurements allow the doctor or other medical practitioner to determine if the treatment has been effective by determining if unwanted bladder contraction is continuing to occur and/or what hydrostatic pressure in the bladder causes such contraction. Multiple measurements may be taken over the course of the procedure (including before, during and after) to determine the effectiveness of treatment. For treatments involving use of the neuromodulation signal, the physician can use the pressure measurement to assess the effectiveness of one or both of the waveform of the neuro-modulation signal as well as the placement of the electrode to deliver the signal.

In related embodiments, pressure measurements can be made using embodiments of the pressure measurement catheter 10 described herein to assess the effectiveness of treatment for overactive bladder comprising the delivery of pulsed electrical signals to the patients foot from a plurality of electrodes placed on the patient's foot (e.g., on the plantar or dorsal side adjacent metatarsal bones). Specifically, pressures in the bladder (and/or urethral sphincter) can be measured to determine a micturition volume threshold in the bladder and the effectiveness of the delivered pulsed electrical signals in increasing that threshold. The pressure measurements can be used to assist in one or more of electrode placement on the patient's foot and/or tuning or fine tuning of the electrical signal waveform (e.g., in terms of pulse width, frequency, and amplitude) to optimize increases in the patients micturition volume threshold. As described above, micturition volume threshold (MVT) is the volume of fluid in the bladder which results in a contraction and subsequent voiding of the bladder. As such, an increase in the MVT is one indication of the effectiveness of treatment in reducing an overactive bladder. For example, MVT can be determined using an embodiment of the pressure measurement catheter 10 to fill the bladder with fluid (e.g., through an irrigation lumen) and then monitoring the delivered volume at which bladder contraction and voiding occurs. Typically, the stimulating electrical waveform comprises a pulsed signal having a frequency ranging from about 1 Hz to 500 Hz a voltage ranging from about 1 V to 50 V and pulse width from about 0.1 to 3 ms. Pressure measurements can be made using embodiments of the invention to tune and/or fine tune one or more of these signal parameters so as optimize the increase in micturition volume in the bladder in response to the delivery of the electrical signals.

The foregoing description of various embodiments of the invention has been presented for purposes of illustration and description. It is not intended to limit the invention to the precise forms disclosed. Many modifications, variations and refinements will be apparent to practitioners skilled in the art. For example, the embodiments of the pressure measurement catheter can be modified in one or more of size, shape or other property for various pediatric and even neonatal applications.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. A catheter for simultaneously measuring pressure at multiple locations in the urinary tract of a patient, the catheter comprising:
  a catheter body having a proximal and distal end and a plurality of lumens including at least a first, second and third lumen;
  the plurality of lumens configured so as to minimize an effect of a pressure change in one lumen of the plurality of lumens on a pressure in another lumen of the plurality wherein, each lumen of the plurality of lumens has sufficient stiffness or hoop strength such that a pressure change in one lumen of the plurality of lumens causes a 5% or less pressure change in another lumen of the plurality of lumens;

an adaptor coupled to the proximal end of the catheter body, the adaptor including a plurality of ports including at least a first, second and third port for fluidic coupling to the plurality of lumens;

a first pressure sensor fluidically coupled to the first lumen, the first pressure sensor configured and positioned on the catheter body to be positioned and measure pressure in a urethra of the patient;

a second pressure sensor fluidically coupled to the second lumen, the second pressure sensor configured and positioned on the catheter body to be positioned and measure pressure in a bladder of the patient; and an expandable retention member fluidically coupled to the third lumen and positioned on the catheter body between the first and second pressure sensors, the expandable retention member configured when in an expanded state to retain the catheter body at selected location in the urinary tract in response to a physiological force exerted on at least a portion of the catheter.

2. The catheter of claim 1, wherein the at least a portion of the catheter includes at least one of the retention member, the catheter body, or the second pressure sensor.

3. The catheter of claim 1, wherein the physiological force corresponds to a hydrostatic pressure from fluid in the patient's bladder.

4. The catheter of claim 1, wherein the physiological force corresponds to a force resulting from a contraction of at least of the patient's bladder or a urethral sphincter of the patient.

5. The catheter of claim 1, wherein the retention member is configured to retain the catheter body in a selected position in the urinary tract during a contraction of at least one of the bladder or the urethra.

6. The catheter of claim 1, wherein the retention member is configured to retain the catheter body in a selected position in the urinary tract to keep the second pressure sensor positioned in the bladder and the first sensor positioned in the urethra in response to hydraulic pressure exerted on at least a portion of the catheter.

7. The catheter of claim 1, wherein the expandable retention member comprises an expandable balloon.

8. The catheter of claim 1, wherein at least one of the second pressure sensor or the first pressure sensor comprises an expandable member having an expanded and a non-expanded state, wherein the at least sensor is configured to be advanced into the urinary tract in the non-expanded state and then deployed to the expanded state to measure pressure in at least of the urethra or the bladder.

9. The catheter of claim 8, wherein the expandable member comprises an expandable balloon.

10. The catheter of claim 9, wherein the expandable balloon comprises at least of an elastomer, silicone or polyurethane.

11. The catheter of claim 8, wherein the expandable member is configured to retain the at least one sensor in the urethra or bladder when in the expanded state.

12. The catheter of claim 1, wherein at least one of the second pressure sensor or the urethra comprises a strain gauge, a MEMS-fabricated sensor or a manometer.

13. The catheter of claim 1, wherein the first pressure sensor comprises a first section and a second section, the first section positioned to measure pressure at first location in the urethra and the second section positioned to measure pressure at a second location in the urethra.

14. The catheter of claim 13, wherein the first location corresponds to an internal urethral sphincter and the second location corresponds to an external urethral sphincter.

15. The catheter of claim 1, wherein the catheter is adapted to be positioned in a male urinary tract.

16. The catheter of claim 15, wherein the second sensor has a length of about 2 cms and is configured to be positioned on either side of a male urinary sphincter.

17. The catheter of claim 1, wherein the catheter is adapted to be positioned in a female urinary tract.

18. The catheter of claim 17, wherein the second sensor has a length of about 1.5 cms and is configured to be positioned on either side of a female urinary sphincter.

19. The catheter of claim 1, wherein at least one of the plurality of ports is configured to be coupled to a manometer.

20. The catheter of claim 1, wherein the catheter includes a fourth lumen fluidically coupled to a fourth port for measurement of a temperature in the urinary tract.

21. The catheter of claim 1, wherein the catheter includes a fourth lumen fluidically coupled to a fourth port for flow of irrigation fluid.

22. The catheter of claim 1, wherein the catheter includes a fourth lumen fluidically coupled to a fourth port for drainage of the bladder.

23. The catheter of claim 22, wherein the catheter includes a fifth lumen coupled to a fifth port for flow of irrigation fluid.

24. The catheter of claim 1, wherein the catheter body comprises an elastomer, silicone, or polyurethane, PTFE, polyethylene or PET.

25. The catheter of claim 1, wherein each lumen of the plurality of lumens has sufficient radial rigidity or hoop strength so as to minimize the effect of the pressure change in one lumen of the plurality on a pressure in another lumen of the plurality.

26. The catheter of claim 25, wherein the radial rigidity of each lumen of the plurality of lumens is in the range of about 20 to 100 N/mm.

27. The catheter of claim 26, wherein the radial rigidity of each lumen of the plurality of lumens is in the range of about 50 to 100 N/mm.

28. The catheter of claim 1, wherein each lumen of the plurality of lumens has sufficient stiffness or hoop strength such that a pressure change in one lumen of the plurality causes a 2% or less pressure change in another lumen of the plurality.

* * * * *

UNITED STATES PATENT AND TRADEMARK OFFICE
CERTIFICATE OF CORRECTION

| | | |
|---|---|---|
| PATENT NO. | : 10,542,924 B2 | Page 1 of 1 |
| APPLICATION NO. | : 15/153314 | |
| DATED | : January 28, 2020 | |
| INVENTOR(S) | : Mir Imran and Ben Tranchina | |

It is certified that error appears in the above-identified patent and that said Letters Patent is hereby corrected as shown below:

In the Claims

Column 9, Line 39, Claim 6:
Add – pressure – before "sensor", second occurrence

Column 9, Line 54, Claim 10:
Add – one – before "of"

Column 10, Line 2, Claim 12:
Add – first pressure sensor – before "urethra"
Delete "urethra" before "comprises"

Column 10, Line 15, Claim 16:
Add – pressure – before "sensor"

Column 10, Line 20, Claim 18:
Add – pressure – before "sensor"

Signed and Sealed this
Third Day of August, 2021

Drew Hirshfeld
*Performing the Functions and Duties of the*
*Under Secretary of Commerce for Intellectual Property and*
*Director of the United States Patent and Trademark Office*